United States Patent [19]
Cotten et al.

[11] Patent Number: 5,693,509
[45] Date of Patent: Dec. 2, 1997

[54] ADENOVIRUS FOR DELIVERING FOREIGN DNA INTO HIGHER EUKARYOTIC CELLS

[75] Inventors: Matthew Cotten, Vienna; Ernst Wagner, Langenzersdorf, both of Austria

[73] Assignees: Boehringer Ingelheim International GmbH, Rhein, Germany; Genentech, Inc., South San Francisco, Calif.

[21] Appl. No.: 530,181

[22] PCT Filed: Apr. 6, 1994

[86] PCT No.: PCT/EP94/01065

§ 371 Date: Sep. 29, 1995

§ 102(e) Date: Sep. 29, 1995

[87] PCT Pub. No.: WO94/24299

PCT Pub. Date: Oct. 27, 1994

[30] Foreign Application Priority Data

Apr. 8, 1993 [DE] Germany .................. 43 11 651.5

[51] Int. Cl.$^6$ .................. A61K 48/00; C07K 3/08; C12N 5/00
[52] U.S. Cl. .................. 435/172.3; 435/240.1; 435/240.2; 435/320.1; 514/44; 530/345; 530/358
[58] Field of Search .................. 514/44, 2; 536/23.1; 435/320.1, 172.2, 240.1, 240.2, 240.25; 424/93.1; 800/2; 530/350, 358

[56] References Cited

U.S. PATENT DOCUMENTS 5,192,553   3/1993   Boyse et al. .................. 424/529
5,354,844  10/1994   Beug et al. .................. 530/345

FOREIGN PATENT DOCUMENTS

WO 92/06180   4/1992   WIPO.
WO 94/10323   5/1994   WIPO.

OTHER PUBLICATIONS

Cotten, M., et al., "High-Efficiency Receptor-Mediated Delivery of Small and Large (48 Kilobase) Gene Constructs Using the Endosome-Disruption Activity of Defective or Chemically Inactivated Adenovirus Particles," *Proc. Natl. Acad. Sci. USA* 89(13):6094–6098 (1992).

Wagner, E., et al., "Coupling of Adenovirus to Transferrin-Polylysine/DNA Complexes Greatly Enhances Receptor-Mediated Gene Delivery and Expression of Transfected Genes," *Proc. Natl. Acd. Sci. USA* 89(13):6099–6103 (1992).

Gao et al., Hum. Gene Ther., 4, 1993, 17–24.

Wagner et al., P.N.A.S., 89, 1992, 6099–6103.

Wagner et al., Bioconjugate Chem., 2, 1991, 226–231.

Curiel et al., PNAS, 88, 1991, 8856–8854.

Curiel et al., Human Gene Therapy, 3, 1992, 147–154.

Marshall, Science, 269, 1995, 1050–1055.

Miller et al., FASEB J., 9, 1995, 190–199.

Culver et al., TIG, 10(5), 1994, 174–178.

Hodgson, Exp. Opin. Ther. Pat., 5(5), 1995, 459–468.

*Primary Examiner*—Jacqueline M. Stone
*Assistant Examiner*—Andrew Milne
*Attorney, Agent, or Firm*—Sterne, Kessler, Goldstein & Fox P.L.L.C.

[57] ABSTRACT

Viruses or cells are targeted for selective internalization into a target in vive. A molecule Specific for a receptor on the surface of the target cell is introduced onto the surface of the virus or cell. The modified virus or cell binds the receptor in vive and is internalized by the target cell. The method provides vectors for selective delivery of nucleic acids to specific cell types in vivo and a means to alter the tropism of an infectious agent.

13 Claims, 4 Drawing Sheets

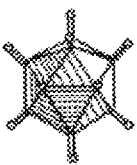
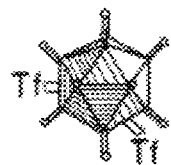
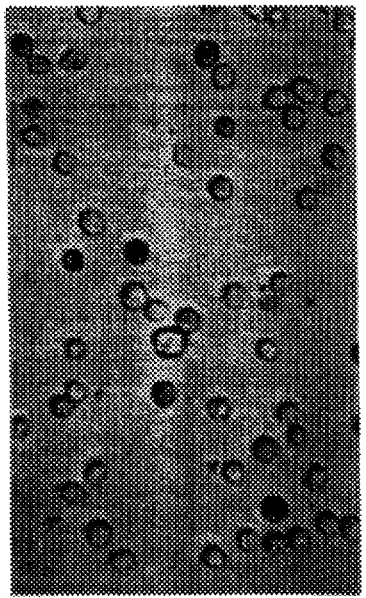
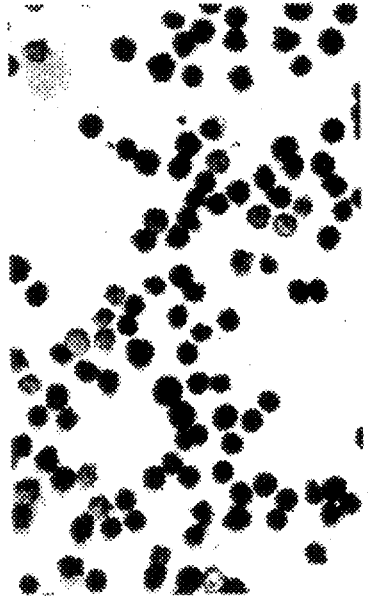
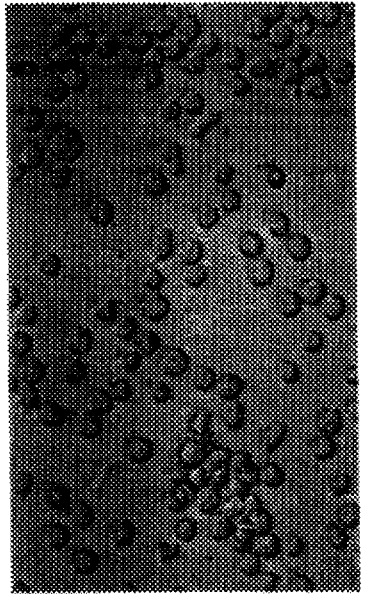
FIG.3A    FIG.3B    FIG.3C

ADENOVIRUS FOR DELIVERING FOREIGN DNA INTO HIGHER EUKARYOTIC CELLS

The invention relates to the introduction of nucleic acids into higher eukaryotic cells.

There is a need for an efficient system of introducing nucleic acid into living cells particularly in gene therapy. This involves delivering genes into cells in order to achieve, in vivo, the synthesis of therapeutically effective gene products, e.g. in order to replace a defective gene in the event of a genetic defect.

For transferring genes into the cells, viral vectors are used, for example, which make use of the efficient entry mechanisms of their original viruses. By this is meant viruses in which the gene to be expressed in the cell has been integrated in the genome by recombinant methods. This strategy was used in the construction of recombinant retroviral and adenoviral vectors, in order to achieve a highly effective gene transfer in vitro and in vivo. The most advanced technologies for using nucleic acids in the course of gene therapy use retroviral systems for delivering genes into the cell (Wilson et al., 1990; Kasid et al., 1990). Therefore, methods have already been developed for expanding the applicability of the retroviral systems or for making them specific to a defined cell population, e.g. by altering the tropism of the viruses.

Roux et al., 1989, as well as French Patent Application 2 649 119, described a system which changes the tropism of retroviruses by means of bifunctional conjugates which contain on the one hand an antibody against the virus coat and, on the other hand, a specific cell membrane marker for the target cell and thus establish a connection between the virus and the host cell.

The approach suggested by Goud et al., 1988 is also based on the principle of bifunctional conjugates. These conjugates are a construction of two monoclonal antibodies, one of which is directed against the human transferrin receptor whilst the other is directed against the gp70 coat protein of the Moloney retrovirus. With these conjugates the retrovirus was able to penetrate into the target cells but could not replicate therein.

The method of changing the tropism of a virus described in WO 92/06180 consists in providing the surface of a virus with a molecule which binds to a surface receptor of the target cell, thereby giving the virus a specificity for the target cell which would not naturally be present. WO 92/06180 describes the modification of a retrovirus and hepatitis virus B with carbohydrate molecules which bind to the asialoglycoprotein receptor.

For use in gene therapy, recombinant adenoviruses have recently come to replace recombinant retroviruses to an increasing extent (Berkner, 1988; Stratford-Perricaudet et al., 1990; Rosenfeld et al., 1991; Rosenfeld et al., 1992; Stratford-Perricaudet et al., 1992).

Adenoviral vectors have the advantageous ability to penetrate into non-dividing cells and absorb a foreign DNA sequence to an extent of up to 8.5 kb. Moreover, the adenovirus particles can be thoroughly purified without losing any stability and are produced in titres greater than $10^{11}$ PFUs/ml.

One restriction on the use of the recombinant vectors derived from the adenoviruses Ad2 and Ad5 consists in their limited ability to penetrate into blood cells. However, blood cells are a preferred target for applications in gene therapy since they are readily available and can be re-introduced into the patients, in addition, the methods of obtaining and cultivating blood cells are well established. The reason for the poor activity of the adenoviral vectors in blood cells lies in the obviously small number of receptors for adenoviruses on these cells (Horvath and Weber 1988; Silver and Anderson, 1988). Whilst the binding of the virus to these cells is reduced by a factor of two to five, the internalisation of the bound virus is even less. The low number of receptors at the outset would thus appear to be accompanied by a greatly reduced internalisation of the available receptors.

Recently, in a number of studies, it was proposed to use non-recombinant adenoviruses for gene transfer with DNA complexes by means of receptor-mediated endocytosis, in view of the ability of adenoviruses to release the contents of endosomes. The use of adenoviruses brings about an increase in the efficiency of gene transfer by avoiding the breakdown of the DNA complexes in the lysosomes internalised in the cell (Curiel et al., 1991; Curiel et al., 1992a; Zatloukal et al., 1992; Cotten et al., 1992; Wagner et al., 1992; Curiel et al., 1992b; Yoshimura et al., 1993; WO 93/07283). It was proposed, inter alia, to modify the adenoviruses by binding to polylysine. The adenovirus-polylysine-conjugates may be complexed together with conjugates of transferrin-polylysine with DNA, thereby obtaining ternary transferrin-polylysine/adenovirus-polylysine/DNA complexes (Wagner et al., 1992). In the course of this study it was found that K562 cells showed only very low expression rates for the imported reporter gene in the presence of free adenovirus on transfection with transferrin-polylysine-conjugates, whereas polylysine-coupled adenovirus, complexed to the reporter DNA together with transferrin-polylysine in order to form a ternary complex, achieved very good results. This phenomenon can presumably be put down to the fact that the internalisation of the DNA complexes in blood cells having a small number of adenovirus receptors occurs via the transferrin receptor, of which the blood cells have a plentiful number.

Adenoviruses cannot penetrate into cells which do not have adenovirus receptors or do not have sufficient for efficient internalisation, or, as is important for use in vivo, are prevented by the fact that the binding sites of the virus are blocked, e.g. by an antibody.

The objective of the present invention was to give adenoviruses the ability to penetrate efficiently into cells into which they cannot normally penetrate, whilst retaining their capacity for gene expression and/or their endosomolytic properties.

The invention thus relates to a virus for transporting foreign DNA into higher eukaryotic cells, the surface of which is modified with a ligand for a surface receptor of the target cell in such a way that it binds to the cell and is internalised in such a way that the foreign DNA is expressed in the cell. The virus is characterized in that it is an adenovirus and the ligand is transferrin.

It has, surprisingly, been found that foreign DNA can be internalised and efficiently expressed, by means of transferrin-modified adenovirus, in blood cells which are not susceptible to the absorption of non-modified adenovirus. When a cell is infected by a virus a number of complex processes take place which follow different strategies for the different viruses. Since the productive entry of a virus involves numerous events connected to the binding of the virus to its receptor, whilst, for example, any change of shape which the virus undergoes on binding to its receptor may be an essential prerequisite for the process of internalising and replication, it is not possible to predict whether the correlation between the events necessary for infection is maintained when the virus undergoes modifications.

The entry of transferrin-modified adenovirus via the transferrin receptor (B) compared with the entry of the unmodified virus (A) via its receptor is diagrammatically shown in FIG. 1.

The transferrin-modified adenoviruses according to the invention may be used in order to improve, in trans, the uptake of transferrin-polylysine/DNA complexes into cells which have transferrin receptors but no adenovirus receptors, or not enough adenovirus receptors. When used in trans, the modified adenovirus is applied together with transferrin-polylysine/DNA complexes, to the cells which are to be transfected, in order to be absorbed into the cell together with the DNA complexes and to bring about the release of the DNA complexes from the endosomes by means of its endosomolytic qualities (Curiel et al., 1991).

The modified adenovirus may also be used, as a constituent of ternary or combined complexes (Zatloukal et al., 1992), in order to increase the efficiency of these complexes. For this purpose the transferrin-modified virus according to the invention is combined with a polylysine/DNA complex, for example by means of a biotin-streptavidin bridge, whilst optionally the polylysine is also conjugated with transferrin. As a result of the transferrin coupled to the adenovirus, the virus in this case takes on the function of an internalising factor for the combined complex, in addition to its endosomolytic function, in cells which have transferrin receptors.

The adenovirus conjugates according to the invention may be used in any applications in which adenoviruses are used to bring about an increase in gene transfer (Curiel et al., 1991; Curiel et al., 1992a; Zatloukal et al., 1992; Cotten et al., 1992; Wagner et al., 1992; Curiel et al., 1992b; Yoshimura et al., 1993).

In one embodiment of the invention the adenovirus is a recombinant adenovirus, i.e. an adenovirus which contains foreign sequences integrated in its genome by means of recombinant methods. The sequences of primary interest are those whose expression in the target cell brings about a desired biological effect, e.g. DNA, which replaces a defective gene. In this embodiment the present invention has the advantage of overcoming the limited tropism which the otherwise successful use of recombinant adenoviruses has for gene therapy, and making the system more widely applicable.

For the virus conjugates according to the invention there is no restriction whatever as to the adenovirus components; any adenoviruses which have on their surface a group capable of binding to transferrin are suitable, e.g. the adenoviruses described by Berkner, 1988; Stratford-Perricaudet et al., 1990; Rosenfeld et al., 1991; Rosenfeld et al., 1992; Stratford-Perricaudet et al., 1992, which were proposed as vectors for delivering DNA into the human cell, especially for gene therapy, may be modified in order to deliver DNA selectively into the target cell in vivo or ex vivo.

With regard to use in humans, human transferrin is used, in particular, as the transferrin component. Transferrin is an iron transporting protein which is absorbed into the cell very efficiently by receptor-mediated endocytosis, as a result of which it has already been used as a transporting vehicle for numerous applications, e.g. for transporting toxins, lower molecular substances or genes into the cell in the form of various conjugates. The process which takes place during the internalisation of transferrin by its receptor differs from other ligand/receptor pairings, inter alia, by the fact that the transferrin receptor is recycled with a high turnover.

With regard to foreign DNA there are no restrictions of any kind imposed by the present invention; the DNA may be any gene or a plasmid construct which contains, for example, elements coding for inhibiting RNA. Sequences which are effective in gene therapy are known in the art; examples of sequences which are currently regarded as therapeutically promising can be found in the summary published by Anderson, 1992, inter alia.

The invention further relates to a process for introducing foreign DNA into human cells which have no or very few adenovirus receptors or in which the adenovirus receptors are wholly or partly blocked, wherein the cells are treated with the virus according to the invention in a suitable formulation ex vivo or in vivo.

In particular, the cells are blood cells.

The requirements imposed on the formulation in which the modified viruses according to the invention are administered are defined by the particular application; anyone skilled in the art can study the relevant pharmaceutical manuals (e.g. Remington's Pharmaceutical Sciences, 1980) to find the numerous carriers and additives which are used for the formulation; the essential requirement is that the formulation does not affect the transporting function of the virus-transferrin conjugate according to the invention or impair the bioavailability of the protein expressed in the cell.

The virus may be [bound] to transferrin in a manner known per se for coupling peptides, but preferably the adenovirus is bound to transferrin via the carbohydrate side chains of the transferrin. This type of binding is described for transferrin-polylysine conjugates in DE-A1 41 150 38, the disclosure of which is specifically mentioned hereby.

Surprisingly, it has been found that this type of binding is highly suitable for the modification of adenoviruses with transferrin in order to introduce foreign DNA into cells which would otherwise be inaccessible or insufficiently accessible to the transporting vehicle adenovirus.

A prerequisite for the ability of the virus to couple to the carbohydrate side chains of transferrin is the presence of amino groups on the surface of the virus. Without wishing to be tied down to this theory, it ought to be advantageous that the carbohydrate side chain of the transferrin forms a natural spacer between transferrin and the virus. This ought to preserve, on the one hand, the binding and internalising ability of the transferrin, and the endosomolytic activity of the adenovirus on the other hand, which is of importance in the use of the conjugates according to the invention as ingredients in combined complexes.

A preferred process for preparing the adenovirus-transferrin conjugates according to the invention, which is also a subject of the present invention, consists in oxidizing transferrin under mild conditions into a form which contains aldehyde groups in the carbohydrate moiety and coupling the oxidized transferrin with the adenovirus under reducing conditions.

Preferably, periodate and especially sodium periodate is used as the oxidizing agent for the oxidizing step in which terminal sialic acids of the carbohydrate chains of the transferrin are oxidized into the aldehyde form.

Suitable substances for creating reducing conditions during the coupling of the aldehyde form of the transferrin with the adenovirus are reducing agents which selectively reduce Schiff's bases under mild conditions. In the process according to the invention, sodium cyanoborohydride or tertiary butylaminoborane are preferred for use as reducing agents.

The process is preferably carried out at low temperatures, particularly 0° C. up to ambient temperature.

The mechanisms of the individual reaction steps are well known to the average person skilled in the art; it is therefore within his capabilities to adapt the conditions for the individual steps of the process to the individual requirements. In certain instances it may be desirable to give the virus particle a smaller number of transferrin molecules than in the experiments carried out within the scope of the present invention, in order to achieve an optimum equilibrium between the internalising quality and endosomolytic properties. Modified adenovirus particles with different amounts of transferrin bound thereto may be obtained by empirically altering the ratio of adenovirus to reagent.

SUMMARY OF THE FIGURES

FIGS. 3A, 3B and 3C: Expression of β-galactosidase in K562 cells after transfection with recombinant adenovirus. 3A: Non-modified adenovirus. 3B: Transferrin-modified adenovirus. 3C: Control (uninfected cells).

Figure 1A:
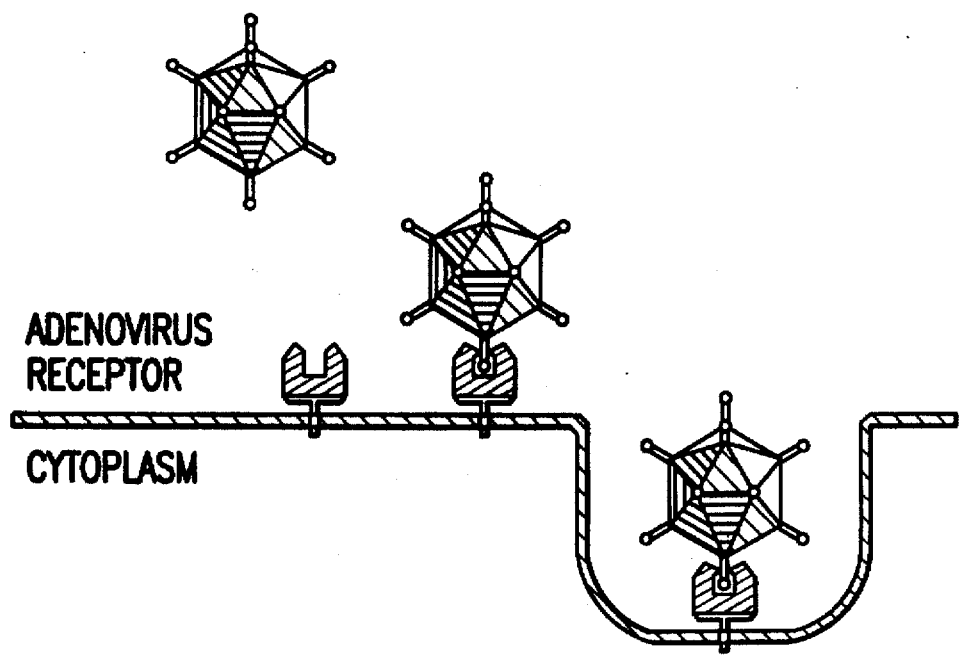
FIGS. 1A, and 1B: Schematic representation of the entry of the virus into the cell. 1A: Non-modified adenovirus. 1B: Transferrin-modified adenovirus.
Figure 1B:
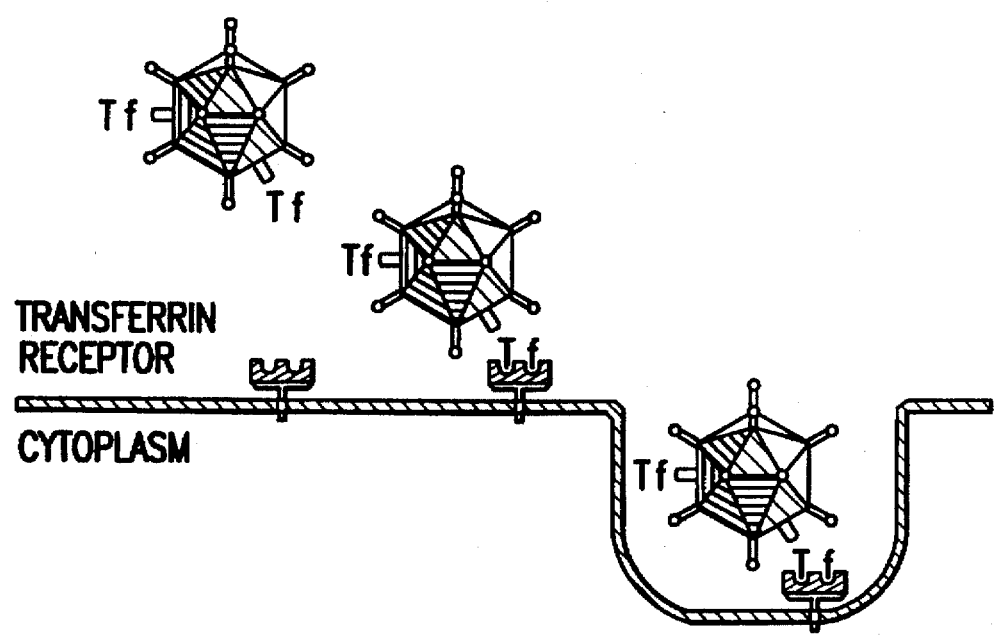

The invention is illustrated by means of the following Example:

EXAMPLE a) Adenovirus Preparation $5 \times 10^6$ 293 cells (ATCC No. 1573; Graham et al., 1977) were cultured in 175 cm² flasks with 60 ml DMEM medium plus 10% FCS and 1% glutamine with the addition of antibiotics (penicillin, streptomycin) for 3 days at 37° C. and 5% $CO_2$ until about $2 \times 10^7$ cells were obtained, which were about 80–100% confluent. The medium was then removed and the cells were infected with adenovirus Ad.RSVβgal (E1-, E3-defective adenovirus type 5 which carries the E. coli galactosidase gene under the control of the RSV promoter/enhancer; Stratford-Perricaudet et al., 1992) (about $2 \times 10^9$ particles in 5 ml of medium with 2% FCS). After about 2 days incubation at 37° C. the cells had swollen and had detached themselves almost entirely from the bottom. The cells were then centrifuged for 10 minutes at 3,000 rpm in a Sorvall GSA Rotor, the cell pellets were transferred with PBS into a 50 ml test tube and centrifuged for 10 minutes in a Heraeus centrifuge at 1,000 rpm. The pellet was taken up in 2 to 3 times its volume of 10 mM HEPES/1 mM EDTA (HE), flash-frozen in liquid nitrogen and stored at −70° C. In order to open up the cells they were subjected to four freezing and thawing cycles (liquid nitrogen/37° C. water bath) and centrifuged for 10 minutes (Heraeus, 4,000 rpm). The cell lysate was then subjected to ultracentrifugation (vTI-50 47,000 rpm/1 h/20° C.; CsCl density gradient: 20 ml 1.33 g/cm³ CsCl in HE, resting on 10 ml of 1.45 g/cm³ CsCl in HE, covered with 10 ml of cell lysate). The opalescent virus band was collected and subjected to a second ultracentrifugation (vTI-50 63,000 rpm/4 h/20° C.; CsCl equilibrium gradient: 2.5 ml 1.33 g/cm³ CsCl in HE, mixed with 2.5 ml virus band). For each cell culture flask, $1–3 \times 10^{11}$ virus particles were obtained which were stored at −70° C. with 40% (v/v) glycerol. The virion concentration was determined via the protein content by means of Bradford assay (BSA, fraction V, BMB as standard), using the ratio 1 mg/ml virus protein=$1.34 \times 10^{12}$ virus particles (Lemay et al., 1980).

b) Modification of the Adenovirus with Transferrin

A solution of 105 mg (1.30 μmol) of transferrin (human, Sigma) in 1 ml of 30 mM sodium acetate buffer (pH 5) was subjected to gel filtration on a Sephadex G-25 PD10 column (Pharmacia), using the same buffer. The 2 ml of solution obtained, which contained 80 mg (1.0 μmol) of transferrin (the transferrin content being determined by UV measurement at 280 nm and ninhydrin assay), were concentrated down to 1 ml in a Speedvac (Savant), cooled to 0° C. and treated with 50 μl of 30 mM sodium acetate buffer (pH 5), containing 1.1 mg (5 μmol) of sodium periodate. The mixture was left to stand for 90 minutes in an ice bath in the dark. Then another gel filtration was carried out Sephadex G-25 PD10 column, Pharmacia, 150 mM NaCl, 10 mM HEPES, pH 7.3), whereupon 1 ml of a solution containing 66 mg (0.82 μmol) of oxidized transferrin was obtained (the content of oxidized aldehyde-containing form of transferrin was determined by staining with anisaldehyde reagent as described by Wagner et al., 1991). Some of the modified transferrin solution (0.6 ml; 0.5 μmol) was added quickly to a solution containing 25 μg (based on protein) of adenovirus in 300 μl of HBS. After 1 hour at ambient temperature, a solution of 1 mg (15 μmol) of sodium cyanoborohydride was added. After 24 hours at ambient temperature the transferrin-conjugated adenovirus was purified to remove excess free transferrin, by diluting the virus with an equal volume of HBS (150 mM NaCl, 20 mM HEPES, pH 7.4) and centrifuging the material through a CsCl step gradient. About 1.5 ml of the modified virus were underlaid in a vTi-65 tube (Beckman) with 3 ml of 1.31 g/cm³ CsCl and 1 ml of 1.45 g/cm³ CsCl (both CsCl solutions in 1 mM EDTA, 20 mM HEPES, pH 7.4). The sample was centrifuged for 1 hour at 63,000 rpm in a vTi-65 rotor (Beckman). The opalescent virus band was harvested, diluted with an equal volume of HBS and subjected to a second, identical CsCl gradient purification. Alternatively, the first virus band was adjusted to 5.5 ml with 1.33 g/cm³ CsCl, 20 mM HEPES, 1 mM EDTA, pH 7.4 and the sample was centrifuged to equilibrium (4 hours, 63,000 rpm, vTi-65 rotor). The purified modified virus was harvested, diluted with an equal volume of 96% glycerol (Fluka) and stored at −70° C. until use. A parallel coupling was carried out with iron-free transferrin; the purified virus as mixed with 1 μl of 1 mM iron (III) citrate buffer, pH 7.5.

c) Quantitative Measurement of the Transferrin Bound to Adenovirus

Figure 2:
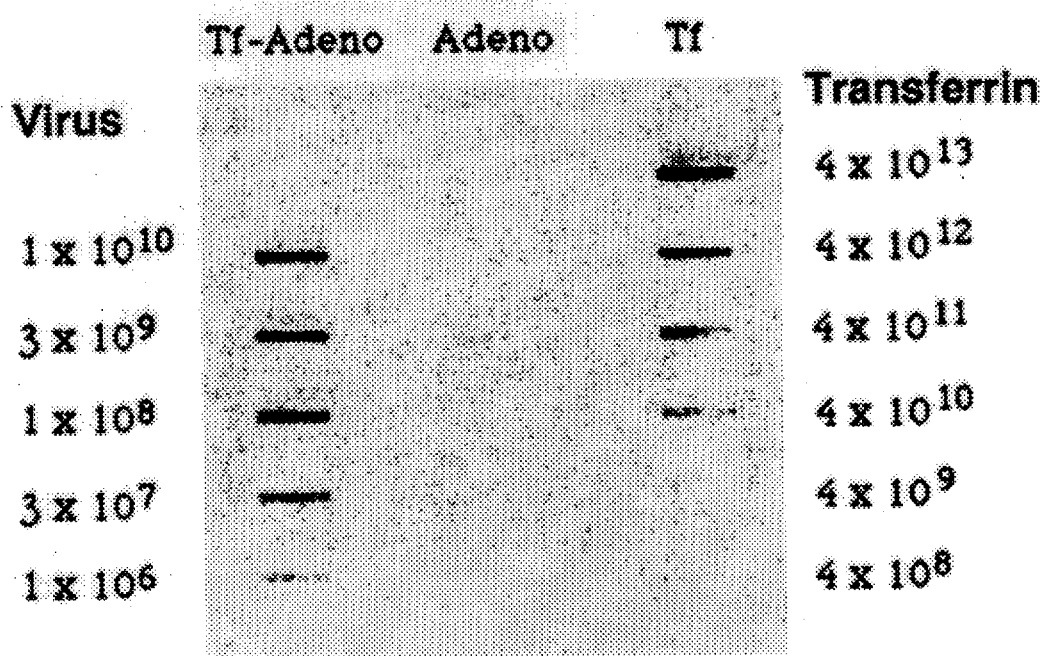
FIG. 2: Quantification of the transferrin bound to adenovirus on a nitrocellulose membrane blot.

Serial dilutions of transferrin-modified adenovirus, non-modified adenovirus and transferrin standards (each in HBS; the number of virus particles or transferrin molecules applied can be found in FIG. 2) were bound to a nitrocellulose membrane (Schleicher & Schuell, 0.1 mm pore size). The blot was pre-hybridised overnight at 4° C. with 3% (w/v) powdered skimmed milk in HBS (10 ml). The transferrin content of each sample was determined by exposing the membrane for 4 hours at ambient temperature to a mouse antibody which recognises human transferrin (Chemicon MAB 033-19/1, dilution 1:2000 in HBS/milk, 10 ml), and then (after 2 hours washing with 4×130 ml of HBS/milk) exposed for 1 hour to a $^{125}$I-labelled second antibody (sheep-anti-mouse-Ig, Amersham, Catalogue No. L52215, 2 μCi, in 20 ml of HBS/milk). The phosphoimager analysis of the membrane shows the presence of transferrin in the probes with modified adenovirus, but no signal in the non-modified adenovirus. Comparison of the signals obtained with the modified virus with the transferrin standards makes it possible to determine the quantity of transferrin bound to a virus particle. It was found that $3 \times 10^9$ virus particles give a signal which is comparable with that of $4 \times 10^{12}$ transferrin molecules. This shows that approximately 1,000 transferrin molecules are bound to an adenovirus particle. The association of the transferrin molecules with adenovirus particles by two CsCl density gradients indicates covalent bonding between capsid proteins of the virus and the transferrin molecule. This also accords with the results of an analysis of virus capsid proteins using SDS-PAGE, which showed that the majority of the coupled transferrin is bound to the hexone.

d) Transfection of K562 Cells with Transferrin-Modified Recombinant Adenovirus Containing the β-Galactosidase Gene as Foreign DNA K562 cells (ATCC No. CCL 243) were cultured in suspension in RPMI 1640 medium (Gibco BRL) plus 10% FCS, 100 units/ml penicillin, 100 µg/ml streptomycin and 2 mM glutamine. 20 hours before transfection the cells were transferred into fresh medium containing 50 µM of desferrioxamine (Cotten et al., 1990) in order to increase their number of transferrin receptors. The transfections were carried out at a density of 250,000 cells/ml in the same medium (plus 50 µM desferrioxamine). The same amounts (3,000 virus particles/cell up to 300 virus particles/cell) of either unmodified adenovirus (Ad.RSVβgal) or modified adenovirus (Tf-Ad.RSVβgal) were applied to the K562 cells. 48 hours after transfection, about 25,000 cells in a volume of 100 to 200 µl were transferred into the wells of a round-bottomed 96-well plate and centrifuged for 10 minutes at 800 rpm in a Beckman GH 3.7 rotor. The supernatant was carefully removed and replaced with 100 µl of 0.5% glutardialdehyde in HBS. The cells were dispersed by pipetting and then centrifuged again. The fixing agent was then removed and the cells were washed. Then 200 µl of staining solution (10 mM phosphate buffer pH 7.0, 150 mM NaCl, 1 mM $MgCl_2$, 3.3 mM $K_4Fe(CN)_6 3H_2O$, 3.3 mM $K_3Fe(CN)_6$ and 0.2% 5-bromo-4-chloro-3-indolyl-β-galactopyranoside) were incubated at 37° C. for 20 minutes to 3 hours (Lim and Chae, 1989). The cells were incubated for 5 hours at 38° C., then washed twice, transferred into flat-bottomed wells of a 96-well plate and photographed.

The results of the transfections are shown in FIGS. 3A–3C: it has been found that, at the highest ratio of virus to cell, the non-modified virus is capable of transducing the cells with a performance of about 5%. However, at the same ratio of virus to cell, the transferrin-modified virus transduces more than 90% of the cell population, and the actual quantities of β-galactosidase produced per cell are also higher. Control tests showed that both non-modified and transferrin-modified adenovirus were able to penetrate into HeLa cells with the same performance level.

Figure 4:
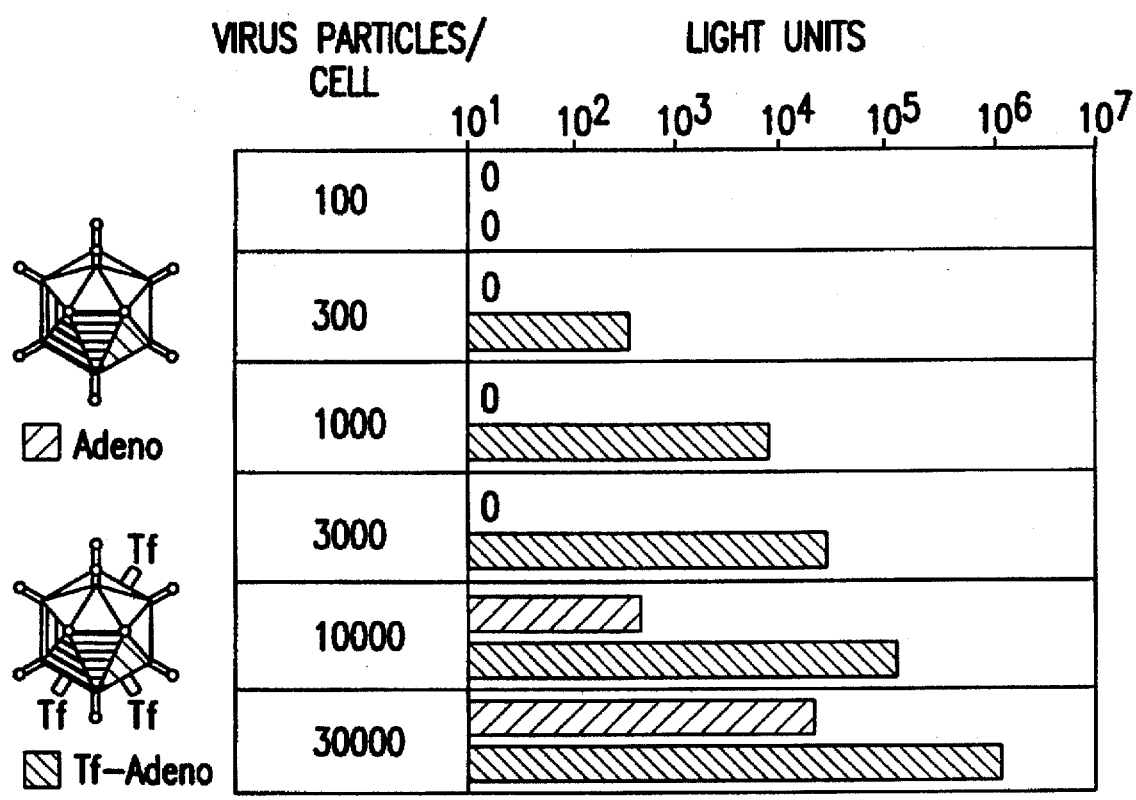
FIG. 4: Quantitative comparison by means of luminometry of the gene transfer into K562 cells.

Additionally, the β-galactosidase activity was analysed by luminometry using the method described by Jain and Magratz, 1991. To do this, K562 cells were cultured for 18 hours in RPMI/10% FCS, containing 50 µM desferrioxamine. Immediately before infection the cells were placed in fresh medium containing desferrioxamine (250,000 cells/ml, 50,000 cells per well of a plate with 96 wells). The dilutions of the controls and samples with transferrin-modified adenovirus Ad.RSVβgal were prepared in RPMI/2% heat-inactivated equine serum and aliquots of the virus (50 µl) which contained the number of virus particles per cell specified in FIG. 4, were placed on the cells. After 4 hours at 37° C. the cells were washed in fresh medium (without desferrioxamine). After 24 hours at 37° C., aliquots of 50,000 infected or control cells were collected by centrifuging for luminometric measurement, taken up in 100 µl of 0.25M Tris pH 7.5 and broken up by three freezing/thawing cycles (liquid nitrogen/37° C.). The cell debris was removed by centrifuging (14,000×g, Eppendorf) and aliquots of the supernatant, standardised for protein content, were analysed using the chemiluminescent substrate AMPGD and an Emerald Luminescence Intensifier (Tropix). The results of the measurements are shown in FIG. 4.

Bibliography

Anderson, F. W., 1992, Science 256, 808.

Berkner, K. L., 1988, BioTechniques 6, 616–629.

Cotten, M., Wagner, E., Zatloukal, K., Phillips, S., Curiel, D. T. and Birnstiel, M. L., 1992, Proc.Natl.Acad.Sci. U.S.A. 89, 6094–6098.

Cotten, M., Laengle-Rouault, F., Kirlappos., H., Wagner, E., Mechtler, K., Zenke, M., Beug, H., and Birnstiel, M. L., 1990, Proc.Natl.Acad.Sci. U.S.A. 87, 4033–4037.

Curiel, D. T., Agarwal, S., Wagner, E. and Cotten, M., 1991, Proc.Natl.Acad.Sci. U.S.A. 88, 8850–8854.

Curiel, D. T., Agarwal, S., Romer, M. U., Wagner, E., Cotten, M., Birnstiel, M. L. and Boucher, R. C., 1992a, Am.J.Respir.Cell and Mol.Biol. 6, 247–252.

Curiel, D. T., Wagner, E., Cotten, M., Birnstiel, M. L., Agarwal, S., Li, Ch.-M., Loechel, S. and Hu, P.-H., 1992b, Human Gene Therapie 3, 147–154.

Goud, B., Legrain, P. and Buttin, G., 1988, Virology 163, 251–254.

Graham, F., Smiley, J., Russel, W. C. and Nairu, R., 1977, J. Gen. Virol. 36, 59–72.

Horvath, J. and Weber, J., 1988, J. Virol. 62, 341–345.

Jain, V. K. and Magrath, I. T., 1992, Anal. Biochem. 199, 119–124.

Kasid, A., Morecki, S., Aebersold, P., Cornetta, K., Culver, K., Freeman, S., Director, E., Lotze, M. T., Blaese, R. M., Anderson, W. F. and Rosenberg, S. A., 1990, Proc.Natl.Acad.Sci. U.S.A. 87, 473–477.

Lemay, P., Boudin, M., Milleville, M. and Boulanger, P., 1980, Virology 101, 131–143.

Lim, K. and Chae, C. B., 1989, BioTechniques 7, 576–579.

Rosenfeld, M. A., Siegfried, W., Yoshimura, K., Yoneyama, K., Fukayama, M., Stier, L. E., Paakko, P. K., Gilardi, P., Stratford-Perricaudet, L. D., Perricaudet, M. et al., 1991, Science 252, 431–434.

Rosenfeld, M. A., Yoshimura, K., Trapnell, B., Yoneyama, K., Rosenthal, E., Dalemans, W., Fukayama, M., Bargon, J., Stier, L., Stratford-Perricaudet, L. D. et al., 1992, Cell 68, 143–155.

Roux, P., Jeanteur, P. and Piechaczyk, M., 1989, Proc.Natl.Acad.Sci. U.S.A. 86, 9079–9083.

Stratford-Perricaudet, L., Levrero, M., Chasse, J.-F., Perricaudet, M. and Briand, P., 1990, Hum. Gene Ther. 1, 241–256.

Stratford-Perricaudet, L., Makeh, I., Perricaudet, M. and Briand, P., 1992, J. Clin. Invest. 90, 626–630.

Wagner, E., Cotten, M., Mechtler, K., Kirlappos, H. and Birnstiel, M. L., 1991, Bioconjugate Chemistry 2, 226–231.

Wagner, E., Zatloukal, K., Cotten, M., Kirlappos, H., Mechtler, K., Curiel, D. T. and Birnstiel, M. L., 1992, Proc.Natl.Acad.Sci. U.S.A. 89, 6099–6103.

Wilson, J. M., Danos, O., Grossman, M., Raulet, D. H. and Mulligan, R. C., 1990, Proc.Natl.Acad.Sci. U.S.A. 87, 439–443.

Yoshimura, K., Rosenfeld, M. A., Seth, P. and Cyrstal, R. G., 1993, J. Biol. Chem. 288, 2300–2303.

Zatloukal, K., Wagner, E., Cotten, M., Phillips, S., Plank, C., Steinlein, P., Curiel, D. and Birnstiel, M. L., 1992, Ann.New York Acad.Sci. 660, 136–153.

Remington's Pharmaceutical Sciences, 1980, Mack Publ. Co., Easton, Pa., Osol (ed.).

We claim:

1. A conjugate comprising an adenovirus and transferrin wherein said transferrin is directly linked to the adenovirus.

2. A conjugate according to claim 1 characterized in that the adenovirus and transferrin are joined together via the carbohydrate side chains of the transferrin.

3. A conjugate according to claim 1 characterized in that the adenovirus is an adenovirus of type 2.

4. A conjugate according to claim 1 characterized in that the adenovirus is an adenovirus of type 5.

5. A conjugate according to any one of claims 1-4 characterized in that the adenovirus is a recombinant adenovirus.

6. A conjugate according to claim 1 characterized in that the transferrin is human transferrin.

7. A process for preparing the conjugate according to claim 1 characterized in that transferrin is oxidized under mild conditions to a form which contains aldehyde groups in the carbohydrate moiety and the oxidized transferrin is coupled with the adenovirus under reducing conditions.

8. A process according to claim 7 characterized in that the transferrin is oxidized with periodate.

9. A process according to claim 7 characterized in that the coupling is carried out under reducing conditions in the presence of a substance which selectively reduces Schiff's bases under conditions which are mild for transferrin.

10. A process according to claim 9 characterized in that the coupling is carried out in the presence of sodium cyanoborohydride.

11. An in vitro process for introducing foreign DNA by means of human adenovirus into human cells which have no or only a small number of adenovirus receptors or the adenovirus receptors of which are wholly or partly blocked, characterized in that the cells are brought into contact with a conjugate as described in claim 5.

12. An in vitro process for introducing foreign DNA by means of human adenovirus into human cells which have no or only a small number of adenovirus receptors or the adenovirus receptors of which are wholly or partly blocked, characterized in that the cells are brought into contact with a conjugate as described in claim 1 as a component of a complex in which polylysine is conjugated with the virus and optionally also with transferrin and is complexed with the foreign DNA.

13. A process according to claim 11 characterized in that the cells are blood cells.

* * * * *